United States Patent [19]
Ekström et al.

[11] Patent Number: 5,376,252
[45] Date of Patent: Dec. 27, 1994

[54] MICROFLUIDIC STRUCTURE AND PROCESS FOR ITS MANUFACTURE

[75] Inventors: Björn Ekström; Gunilla Jacobson; Ove Ohman; Hakan Sjödin, all of Upsala, Sweden

[73] Assignee: Pharmacia Biosensor AB, Upsala, Sweden

[21] Appl. No.: 946,332

[22] Filed: Nov. 10, 1992

[30] Foreign Application Priority Data

May 10, 1990 [SE] Sweden ............................ 9001699.9

[51] Int. Cl.⁵ .................. G01N 27/26; G01N 27/447; G01N 30/60; B01D 15/08
[52] U.S. Cl. ......................... 204/299 R; 204/180.1; 73/23.39; 73/61.53; 210/198.2; 210/656
[58] Field of Search .................. 210/198.2, 198.3, 658, 210/656; 73/61.53, 23.39; 204/299 R, 180.1

[56] References Cited

U.S. PATENT DOCUMENTS

| | | | |
|---|---|---|---|
| 3,449,938 | 6/1969 | Giddings | 210/198.2 X |
| 3,503,712 | 3/1970 | Sussman | 55/386 X |
| 3,538,744 | 11/1970 | Karasek | 73/23.39 |
| 4,900,663 | 2/1990 | Wie et al. | 435/7 |
| 4,935,040 | 6/1990 | Goedert | 210/198.3 X |
| 5,116,495 | 5/1992 | Prohaska | 210/198.2 |
| 5,165,292 | 11/1992 | Prohaska | 210/198.2 X |

FOREIGN PATENT DOCUMENTS

| | | | |
|---|---|---|---|
| 0010456 | 10/1979 | European Pat. Off. | |
| 0107631 | 9/1983 | European Pat. Off. | |
| 0347579 | 5/1989 | European Pat. Off. | |
| 376611 | 7/1990 | European Pat. Off. | 204/299 R |
| 64329161 | 8/1991 | Japan | 204/299 R |

Primary Examiner—John Niebling
Assistant Examiner—John S. Starsiak, Jr.

[57] ABSTRACT

The microfluidic structure comprises first and second substantially planar form-stable base layers and an intermediate spacing layer of elastic material, said spacing layer being recessed to define a microcavity or channel system with at least one of said first and second base layers. The structure is produced by moulding the spacing layer, optionally applied to or integral with a first base layer, against a planar mould, and the microcavity or channel system is completed by applying a second base layer, and optionally said first base layer, to the spacing layer.

30 Claims, 5 Drawing Sheets

MICROFLUIDIC STRUCTURE AND PROCESS FOR ITS MANUFACTURE

FIELD OF THE INVENTION

The present invention relates to an improved microfluidic structure which may find use in various fields of application such as various electrophoretic procedures, capillary chromatography, liquid distribution systems and the like, as well as to a process for the manufacture thereof.

BACKGROUND OF THE INVENTION

A recent development of electrophoretic technique is capillary electrophoresis. As with conventional methods of electrophoresis charged molecules may be isolated and determined in an electric field based upon their relative mobilities. A capillary electrophoretic system basically consists of a fused silica capillary having an inner diameter of approximately 25 to 100 microns and which connects two reservoirs filled with a buffer. Separation takes place in the buffer-filled capillary and substances may be detected by UV absorbance or emitted fluorescence by means of a concentrated transverse beam of light passing through the capillary.

In relation to conventional gel electrophoresis the use of a capillary system permits a considerably higher electric field strength due to reduced generation of heat and an improved cooling effect (reduced ratio of cross-sectional to circumferential area). This results in very fast separations with extremely high resolution.

Drawn glass capillary tubes have, however, several disadvantages. Among those may be mentioned the difficulty of providing branched systems as well as the difficulty of creating areas having particular surface characteristics. It is also relatively difficult to manufacture extremely small bore glass tubes. Further, glass capillaries are also unsuitable for parallel channel analyses and only small volumes can therefore be separated, separations for preparative purposes thereby being impractical.

To overcome these disadvantages planar structures have been developed in which a number of trenches or channels are fabricated in parallel. Typically, such a planar structure is produced by etching trenches in a semiconductor substrate, such as a silicon wafer, and then covering the etched surface by a cover plate to complete the electrophoretic channels. Such structures are, however, rather expensive to produce. Further, since the materials used are rigid and hard, it is difficult to provide an adequate sealing between the top edges of the etched trenches and the cover plate. As the etched substrate is most often a semiconductor, the material per se is unsuitable for electrophoretic applications and the channel side-walls must therefore be provided with an insulating surface layer, such as by oxidation or by coating with some other material.

SUMMARY OF THE INVENTION

An object of the present invention is to provide a microfluidic structure suitable for capillary electrophoresis and which is devoid of the above disadvantages and thus is relatively cheap to produce, optionally permitting a disposable type product, may provide branched flow channels, may exhibit local surface characteristics, and provides great freedom in choice of material, e.g. as regards surface, optical and electric properties.

Another object of the present invention is to provide a microfluidic structure which, in addition to capillary electrophoresis, is suitable for other applications such as capillary chromatography, procedures using micro reaction cavities, miniaturized liquid communication units etc.

Still another object of the present invention is to provide a microfluidic structure in the form of a multistorey construction having channels or cavities in several planes to thereby permit the build-up of complex channel or cavity geometries for analyses or reactions.

Another object of the present invention is to provide a microfluidic structure which permits easy detection of substances in the flow system.

A further object of the present invention is to provide a process for the manufacture of the above microfluidic structure.

Thus, in one aspect the present invention relates to a microfluidic structure comprising first and second substantially planar base layers of a form-stable material, and an intermediate spacing layer of elastic material, said spacing layer being recessed to define a micro cavity or channel system with at least one of said first and second base layers.

In another aspect the present invention provides a process for the manufacture of such a microfluidic structure, which process comprises the steps of providing a mould having a planar face with a relief pattern corresponding to the desired spacing layer geometry, including said liquid flow system, applying and moulding a spacing layer material against the mould surface, optionally together or integral with a superposed first base layer, removing the mould from the shaped spacing layer, applying a second base layer to the shaped surface of the spacing layer to complete the liquid flow system therewith, and, if not done previously, applying said first base layer to the opposite surface of the spacing layer.

BRIEF DESCRIPTION OF THE DRAWINGS

The above objects, features and advantages will be apparent from the following description and the appended claims, taken in conjunction with the accompanying drawings, in which:

DETAILED DESCRIPTION OF THE INVENTION

Figure 1:
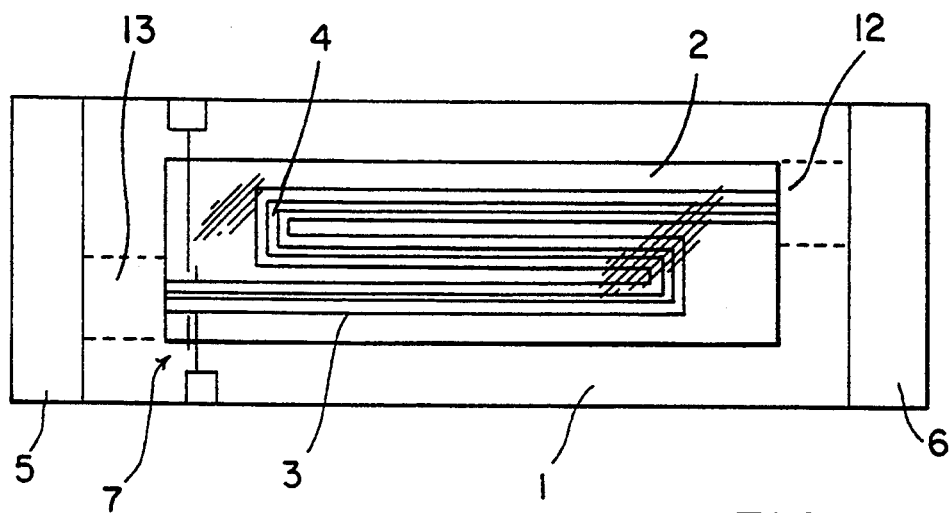
FIG. 1 is a plan view of an embodiment of a capillary electrophoretic plate according to the present invention.

In its simplest form the microfluidic structure according to the present invention comprises two base layers between which an elastic spacing material, which is firmly attached to at least one of the base layers, forms a geometric micro structure defining the desired liquid flow system, e.g. one or more cavities or a labyrinth-like channel.

For the provision of the liquid flow system the spacing layer may be recessed through a part or the whole thickness thereof. In the first case the spacing layer forms the side walls and one of the top and bottom walls of each cavity or channel, one of the base layers forming the other of the top and bottom walls, whereas in the latter case the base layers form the top and bottom walls and the spacing layer forms the side walls. Due to the elasticity of the spacing layer adequate sealing thereof to the respective base layer(s) is obtained.

In a development thereof the structure of the invention includes of a "multi story" sandwich structure having two or more spacing layers separated by base layers, the liquid flow systems in adjacent spacing layers communicating by apertures or bores in the intermediate base layers. In this way e.g. complex flow channel systems may be formed. Such a multi story structure may be formed by piling several base layer/spacing layer assemblies on top of each other.

The base layers should be form-stable, which term, however, herein is to be understood in a relatively broad sense as will be further elucidated below. Therefore, not only non-elastic materials but also moderately elastomeric materials may be contemplated as will readily be appreciated when considering the below stated purpose of and requirements on the base layers. Thus, the purpose of the base layers is, on one hand, to support the spacing layer as well as to form part of the channel or cavity walls, and on the other hand to maintain and ensure the dimensions of the structure in the XY-plane thereof; the XY-plane is that of the base layer plane extension, and Z is the direction perpendicular thereto. Form-stable therefore refers to a material that will give only small and well defined dimensional changes under conditions dictated by the particular application. The base layer surface should have a good surface smoothness to ensure efficient sealing under moderate pressures. This may be implemented, for example, by the base layer being stiff or by using a flexible film placed on a planar and possibly elastic surface. As suitable materials for the base layer, which may be in plate, sheet, foil or film form, may be mentioned glass, metal or plastic, such as polyester, polyethylene terephthalate, e.g. Mylar, fluoroplastic, e.g. Hostaflon. The above mentioned apertures in the base layer, necessary for e.g. sandwich applications, may be accomplished by high precision techniques such as laser drilling or numerically controlled precision machinery.

As mentioned above the purpose of the spacing layer is to build up the side walls of the channels or cavities and provide for the desired elasticity in the Z-direction, i.e. perpendicularly to the plane extension. The material should thus be elastic, i.e. preferably be a rubber or an elastomer. An example of a suitable type of material is silicone rubber. Other specific examples are EPDM rubber and Hostaflon. Depending upon the method used for the manufacture of the base layer/spacing layer assembly, which will be described in more detail below, the spacing layer material should also have satisfactory properties as a moulding material, such as low viscosity and form shrinkage, a suitable curing or hardening principle, e.g. UV-light or other radiation, temperature, etc, as well as a suitable hardness to provide for efficient sealing. The above properties makes it possible to transfer and multiply with great accuracy the exact geometry from precision-made moulds or dies to cheap polymeric materials. Such high precision moulds or dies may, for example, advantageously be fabricated by etching in single crystal materials, as will be described below. As mentioned previously, the elastic or resilient properties of the spacing layer or layers permit a very good sealing between base and spacing layers, or between adjacent spacing layers, to be obtained. The spacing layer (when stabilized) should preferably also have surface properties providing for suitable surface characteristics when joined to a base layer and defining a cavity or channel therewith, e.g. hydrophobic-hydrophobic interaction for applications involving aqueous solutions.

Concerning the basic structure of the invention including two base layers and an intermediate spacing layer, it is readily realized, however, that there are materials that will satisfy at the same time the requirements on both the base layer and the spacing layer. The spacing layer and one or both of the base layers may then be made of the same material. In such a case the spacing layer and one base layer may also be integral as will be further described below. The above described multi-story structure may, of course, also be made up from such integral base layer/spacing layer units. An example of a material that may be used in this respect is Hostaflon.

Preferably, the spacing layer does not fill the whole space enclosed by the two base layers, but only to the extent to provide for sufficient wall thicknesses of the channels or cavities defined thereby. Thus, for e.g. a winding channel the spacing layer material defining it will exhibit the same winding geometry but with a wider cross-section. In this way inter alia a smaller sealing area is obtained, thereby requiring a lower total sealing force to be applied for a given surface pressure.

The elasticity of the spacing layer(s) may also be used to give the structure the function of a pump or valve by variation of a force acting in the Z-direction, i.e. normally to the base and spacing layer planes. The force required to compress the structure to obtain such a pumping action will also be lower the more reduced the spacing layer extension is, as just discussed above.

As stated hereinbefore the required recessing of the spacing layer is, in accordance with the invention, accomplished by forming the spacing layer against a planar mould, e.g. a sheet or plate, which has a moulding surface provided with a relief pattern being the negative of the desired geometric structure to be exhibited by the spacing layer. Such a mould may, for instance, be produced by etching, surface coating, laser processing, electrochemical etching, mechanical processing, or combinations thereof, of a substrate of, for instance, silicon, quartz, ceramic, metal or plastic material, e.g. PMMA or Teflon ®. The mould used for forming the spacing layer may, of course, very well be a replica of an originally manufactured master mould produced therefrom by casting or moulding.

The preferred method of producing such a mould involves etching. The material of choice is then a single crystalline material, like e.g. silicon or quartz, or various group III/V materials, such as e.g. gallium arsenide, i.e. a material which has such a structure/composition that a well-defined surface will be produced by chemical processing in gas or liquid phase, and which has such mechanical/thermal properties that it will withstand the pressures and temperatures required by such forming process. A preferred material is single crystalline silicon.

The etching of a desired relief pattern on the surface may be effected in a manner known per se, i.e. by providing the substrate with an etch stopper layer (usually by oxidation), coating with a photosensitive layer (photoresist), exposing the surface through a mask defining the desired relief pattern, and developing the exposed areas to remove the photoresist therefrom, and then opening the bared etch stopper layer in those areas, removing the remaining photoresist mask, and finally etching the bared substrate surface areas to the desired depth.

The moulding of the spacing layer may be performed in various ways. Thus, for instance, in one embodiment the spacing layer is formed by a compression moulding type procedure, involving impression, or coining or embossing, of the spacing layer material. In this case the spacing layer material, optionally attached to or integral with a base layer, is applied against the mould surface, and the assembly is pressed together by an external force. In case the material is thermoplastic, the viscosity thereof is lowered by increasing the temperature, and the spacing layer relief pattern formed is then made permanent or stabilized by lowering the temperature. Other ways of stabilizing the spacing layer includes cross-linking thereof, e.g. by UV-radiation, a catalyst, heat, etc. In the latter case the spacing layer material may be a thin layer of a cross-linkable liquid, such as a silicone rubber, coated on the surface of the base layer.

In another embodiment the spacing layer is formed by an injection moulding type procedure. In this case the base layer is applied against the mould surface, and the base layer and the mould are pressed together by an external force. A cross-linkable liquid, e.g. a silicone rubber, is then pressed into the mould cavity formed, whereupon it is cross-linked by appropriate cross-linking means, such as UV-light. Alternatively, a thermoplastic polymer melt might be injected to form the spacing layer when stabilized by cooling.

When the hardening or stabilization of the spacing layer is completed, the base layer/spacing layer assembly is removed from the mould. In order to facilitate the release of the formed spacing layer from the mould, the latter is preferably treated with a release agent prior to the moulding operation, e.g. a fluorotenside in liquid phase or a fluoropolymer in gaseous phase.

After removal from the mould the second base layer is applied to the spacing layer to complete the desired cavity or channel system. Optionally this second base layer is covalently or otherwise bound to the spacing layer by suitable means as will be discussed in more detail below.

In order to achieve optimum sealing between the spacing and base layers, the assembly thereof is, at the time of use for the particular application, placed in a clamping means between planar faced clamp members capable of exerting a compressive force on the assembly. Such a clamping means may also be used to make the assembly perform the above mentioned pumping action.

For electrophoretic purposes the second base layer is advantageously provided with contact means, e.g. gold strips, at each end thereof, as well as detector means or at least provisions therefor. In such a case this second base layer is preferably made reusable, whereas the first base layer with attached spacing layer is of disposable type and separable from the second base layer such that after use the latter may readily be provided with a new base layer/spacing layer assembly.

As mentioned above the microfluidic structure of the invention may, of course, advantageously also be designed for other microfluidic purposes than electrophoresis. Among those are e.g. capillary chromatography, micro-reaction cavity procedures, miniaturized liquid communication units, biosensor flow cells, etc. Reaction cavities constructed in accordance with the invention may, for example, be used for various forms of solid phase synthesis, such as peptide or oligonucleotide synthesis, PCR, DNA-solid phase sequencing reactions, just to mention a few.

FIG. 1 illustrates a capillary electrophoretic plate according to the present invention. It includes a first base layer 1, a second base layer 2, and an elastic spacing layer 3 disposed between the two base layers 1, 2. The spacing layer 3 is recessed to define a channel 4. For illustrative clarity only, the base layer 2 is here made transparent (FIGS. 1 and 3).

The base layer 1 is made of a form-stable, i.e. non-elastic or moderately elastic, material, for instance glass, and is at each end portion thereof provided with electrode strips 5, 6, e.g. of gold film. In the illustrated case the base layer 1 is also provided with a conductivity detector means 7 in the form of a pair of e.g. gold electrodes 8, 9 arranged to cross the channel 4 and extending from contact pieces 10, 11, e.g. also of gold, on either side of the base layer.

Figure 3:
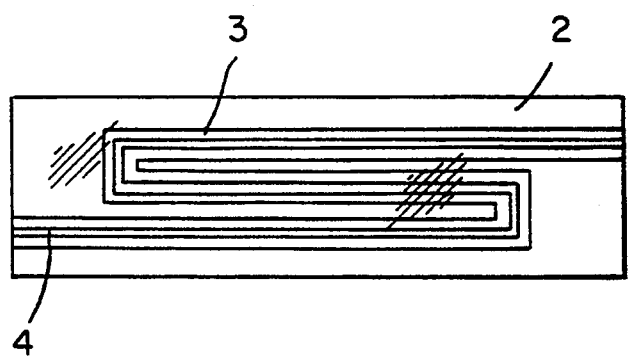
FIG. 3 is a plan view of the other base layer of the structure in FIG. 1 supporting a spacing layer defining an upwardly open liquid channel.

The elastic spacing layer is attached to the second base layer 2, e.g. a polyester film, as shown in FIG. 3. In the illustrated case the spacing layer 3 is a labyrinth-like structure having the channel 4 recess therethrough. In FIG. 3 the spacing layer 3 is attached to the bottom side of the base layer 2, and the channel 4 is therefore open downwardly, whereas the top wall thereof is formed by base plate 2. The spacing layer 3 may, for example, be made of silicone rubber.

The capillary electrophoretic plate as shown in FIG. 1 is formed by applying the base layer/spacing layer assembly of FIG. 3 to the base layer 1. Due to the elasticity of spacing layer 3, efficient sealing against the base layer 1 is obtained. By matching the surface properties, the importance of which has been mentioned above, sufficient adhesion between base layer 1 and spacing layer 3 for them to stick together will be obtained. For certain material combinations gluing may, however, be necessary.

In a specific non-limiting example, with particular reference to the electrophoretic plate in FIG. 1, the base layer is of glass and has a length of 60 mm, a width of 20 mm and a thickness of about 0.5 mm. The spacing layer 3 is made of silicone, General Electric 670 (General Electric Company), with a hardness of 90 shore and has a width of 1 mm. The length of channel 4 defined thereby is 100 mm and its width 250 microns. The channel depth, i.e. the thickness of the spacing layer, is 50 microns and the volume is 1.25 microliters. The electrodes 8, 9, which may be of gold, have a width of 50 microns and a spacing of 50 microns. The base layer 2, which is of polyester, is 12×40 mm and has a thickness of about 0.2 mm.

To perform an electrophoretic separation with the capillary electrophoretic plate shown in FIG. 1 it is placed between two flat surfaces and an appropriate force is applied to hold the plate sandwich sealingly together. The channel 4 is filled with electrophoretic buffer by applying a liquid drop at one end and sucking it into the channel by means of vacuum. A sample is then applied to the channel, optionally by using the resilient structure as a pump or by an enriching ion exchanger zone as will be described below. Buffer soaked filter paper pieces, indicated in FIG. 1 with dashed lines and designated by reference numerals 12, 13, are applied to the respective ends of channel 4 to provide contact between the channel and the contact strips 5, 6, and the electrophoresis voltage from an external source is applied. The separation process is monitored by the detector 7.

Figure 5:
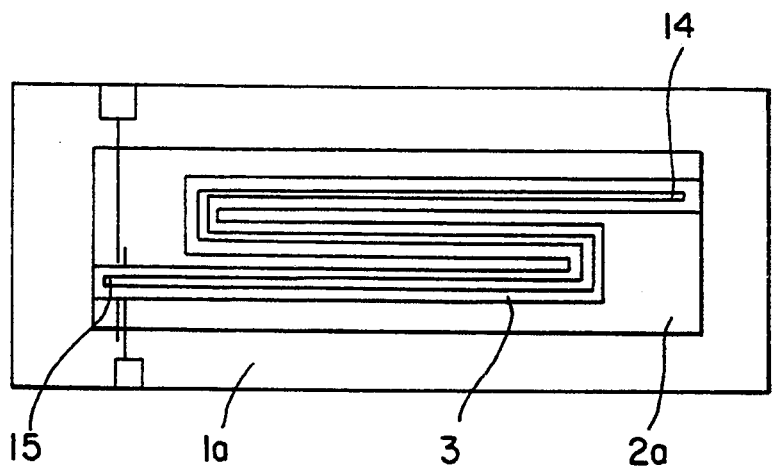
FIG. 5 is another embodiment of capillary electrophoretic plate according to the present invention.

FIG. 5 illustrates a variation of the capillary electrophoretic plate in FIG. 1. In this shown embodiment the channel 4 is closed at each end, and instead the channel opens into apertures 14, 15 made in the upper base layer 2a supporting the spacing layer. There are further no contact strips on the lower base layer, here designated by reference numeral 1a. The buffer may be supplied by e.g. a respective small buffer filled container placed above each aperture 14, 15, into which containers electrodes are immersed for applying the external voltage field.

The spacing layer 3 may, for example, be produced by applying base layer 2 against a planar mould having a relief pattern corresponding to the labyrinth-like spacing layer structure including channel 4. The silicone material is then injected into the mould cavity and the spacing layer formed is subsequently cured by UV irradiation. After removal from the mould the spacing layer 3 supported by the base layer 2 is as shown in FIG. 3.

Figure 6:
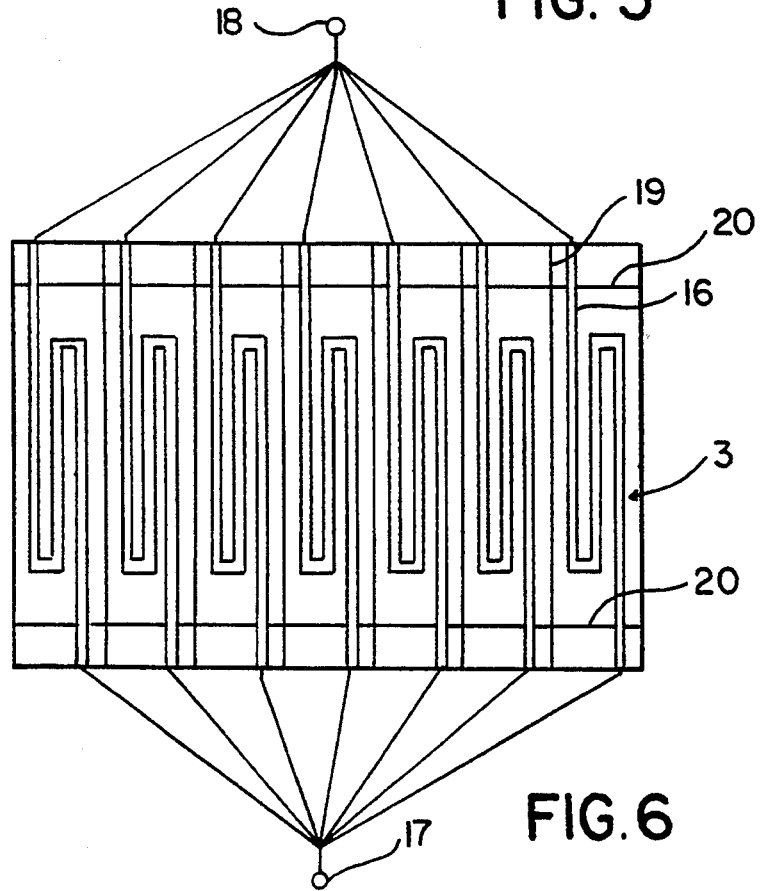
FIG. 6 is a schematic illustration of the manufacture of a number of base layer/spacing layer assemblies corresponding to that in FIG. 3.

A schematic illustration of the production of a plurality of base layers 2 with attached spacing layers 3 as outlined above, e.g. of the materials and dimensions given hereinbefore as a specific example, is represented in FIG. 6. This figure is intended to illustrate a mould surface having a pattern of grooves 16 corresponding to seven spacing layers 3 arranged side by side.

A mould plate exhibiting the desired mould pattern may, for example, be produced as follows:

The surface of a silicon plate is oxidized in an oven at 1100° C. to form an oxide layer of a sufficient thickness, e.g. about 8000 Å. After washing, dehydration in an oven and priming with hexamethylsilane, a photoresist layer is applied by spinning and stabilized by baking. A mask corresponding to the desired groove pattern is then placed upon the plate surface, and the non-covered portions are subjected to light exposure. The exposed photoresist portions are removed by developer solution to bare the oxide layer, and the remaining photoresist mask is hard-baked. The bared oxide is then etched with hydrofluoric acid/ammonium fluoride to expose the silicon (the back-side of the plate being protected, such as by resistant tape) and the photoresist mask is removed by a suitable solvent, such as acetone. The oxide-free silicon areas are then etched by potassium hydroxide solution for a sufficient time to produce the desired depth. The resulting mould surface will exhibit the desired pattern of grooves 16.

To produce the base layer/spacing layer unit 2, 3, a film or sheet of e.g. polyester (here represented as being transparent) is placed upon the mould surface, preferably after having treated the mould surface and film with a release agent. Pressure is then applied, e.g. 4 bars of compressed air, and a cross-linkable liquid, such as silicone rubber (e.g. RTV 670 supplied by General Electric Company) is introduced through the inlet 17 until it emerges at outlet 18. After photo-curing by UV light the base layer sheet is removed from the mould and cut into separate base layer sections (each forming a base layer 2) along lines 19, if not already done prior to application to the mould. Reference numeral 20 indicates transverse stop stripes (not shown in FIG. 1) to prevent buffer in filter papers 8, 9 in FIG. 1 from entering the structure beside the channel.

Figure 7A:
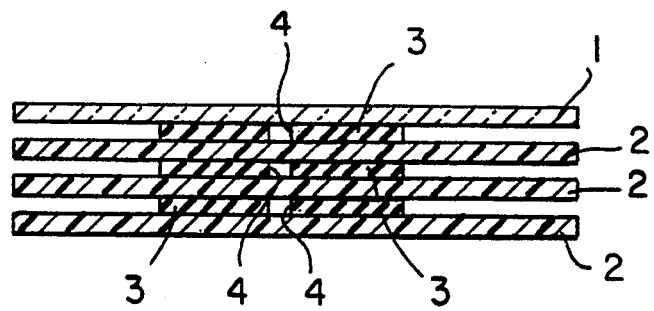
FIG. 7A is a schematic cross-sectional view of a sandwich structure comprising three superposed spacing layers with intermediate base layers.
Figure 7B:
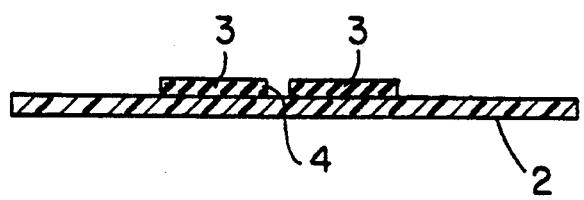
FIG. 7B is a cross-sectional view of one base layer/spacing layer assembly used to build up the sandwich structure.

The structure shown in FIG. 3, including base layer 2 and the spacing layer 3 supported thereby, may be used to build up multi-storey structures as is schematically illustrated in FIG. 7A showing three superposed spacing layer/base layer assemblies according to FIG. 7B. In such manner very complex channel geometries for reactions and analyses may be constructed. The channels of adjacent spacing layers 3 may be connected by bores in the respective base layers, the channel ends then being closed as in base layer 2a in FIG. 5.

In the electrophoretic plate shown in FIGS. 1 and 5 the smaller base layer 2, 2a with attached spacing layer 3, which advantageously is of disposable type, may easily be torn off from the larger base layer 1 provided with detector means 7, whereupon a new base layer/spacing layer assembly 2, 3 may be applied to the base layer 1 which is the more expensive one of the two components.

Figure 4:
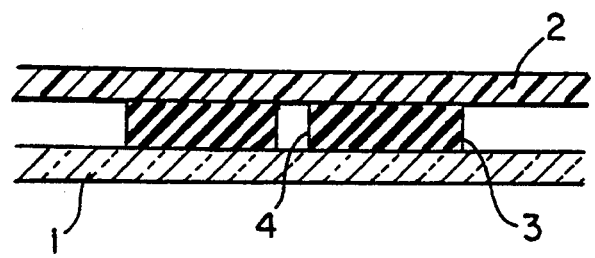
FIG. 4 is a partial cross-sectional view of the structure in FIG. 1.

With reference to the above described structure, and particularly to FIG. 4, the spacing layer 3 and one of the two base layers 1, 2 may be integral, i.e. produced as an integral member from one and the same material. This is schematically illustrated in FIG. 8 wherein reference numeral 21 represents an integral base layer/spacing layer member defining a channel 22, and 23 indicates a second base layer.

The embodiment illustrated in FIG. 8 may e.g. be produced as follows:

A silicon mould plate having the desired relief pattern is first produced as described above, either for a single spacing layer or, preferably, for a plurality of spacing layers as in FIG. 6. A 300–500 $\mu$m Hostaflon film (Hostaflon is a thermoplastic fluoroelastomer supplied by Hoechst AG, Germany) is then applied to the silicon mould surface, optionally after applying a release agent, and a smooth silicon plate, i.e. without any relief pattern, is applied thereabove to sandwich the Hostaflon film between them. Gold coatings are then applied to the outer surfaces of the respective silicon plates. The sandwich is then placed in a pressing means, a pressure (10–50 kg/cm$^2$) is applied and the gold coatings are connected to a voltage source to electrically heat the sandwich to about 150° C. Hereby the Hostaflon film softens and the mould surface pattern is impressed or coined into the plastic film. The voltage source is then disconnected, and the sandwich is allowed to cool. Upon removal from the mould, the resulting base layer/spacing layer unit has a cross-section corresponding to that schematically illustrated in FIG. 8, the spacing layer defining the channels having a thickness of about 50 μm. A non-coined Hostaflon film layer is then applied as the second base layer to complete the structure. This latter film has preferably been heat/pressure treated as above between flat silicon plates to provide a smooth contact surface. Optional liquid communication apertures (indicated as 14 in FIG. 5) are then drilled.

Figure 8:
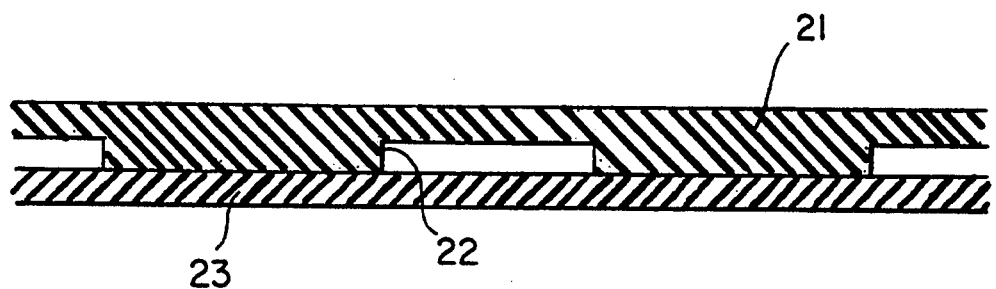
FIG. 8 is a partial cross-sectional view of a structure comprising integral spacing and base layers.
Figure 9:
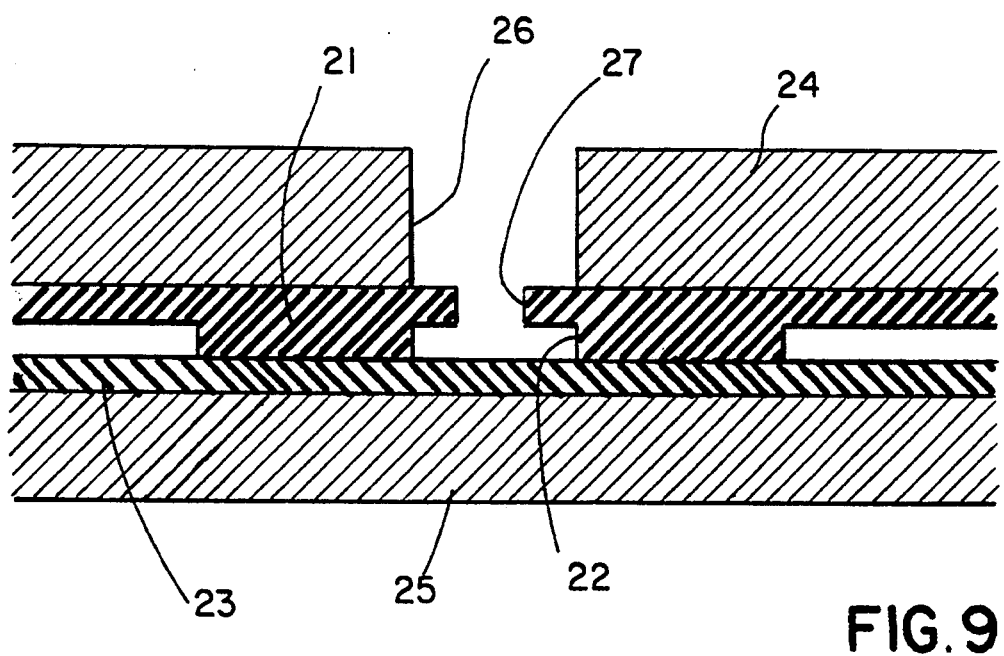
FIG. 9 is a partial cross-sectional view of the structure shown in FIG. 8 placed in a clamping means.

FIG. 9 illustrates the base layer/spacing layer unit 21, 22 of FIG. 8 inserted between clamping members 24, 25 to provide for efficient sealing between the components 21, 22 and 23, respectively. The upper clamping member 24 comprises a container recess 26 communicating with the spacing layer channel 22 through an aperture 27 for the introduction of a fluid into the channel, e.g. buffer in the case of an electrophoretic plate as outlined above in connection with FIG. 5.

It will be realized that in comparison with conventional capillary tube electrophoresis the electrophoretic plate according to the present invention offers several advantages. For example, it will be easy to provide branched inlets and outlets for the capillary structure, which in turn will permit such procedures as isotachophoretic concentration of the sample in a channel section at one end of the capillary channel structure, collection of fractions, and variation of connected electrolytes. Also preparative uses may be contemplated.

The electrophoretic plate having a capillary channel of rectangular cross-section as shown in the drawings and described above is further very advantageous from the viewpoint of detection. Thus, compared with conventional capillary tube electrophoresis it will be much easier to arrange various detector systems, one example being the conductivity detector mentioned above. Another example is the use of a UV detector. In that case the channel may be provided with one or more "windows", i.e. a UV transparent part of the channel bottom (in the illustrated cases base layer 1 or 1a). Such windows may be provided by e.g. metallizing a transparent base layer forming the bottom of the channel to leave a transparent opening or window at the desired site(s). Detection is then performed by illumination with a UV light source. By arranging a sequence of such windows at the inlet part of the channel the amount of sample injected may be determined. Optionally, detectors, such as UV detectors, may be arranged along the whole length of the channel, whereby the migration of the sample substance(s) in the channel may be monitored continuously. In an alternative arrangement a plurality of optical fibres opening towards the channel bottom may be used to direct the light to a detector array for continuous monitoring of the whole or part of the channel. Other types of detectors are, of course, also possible. As is readily realized, the above described detection principles may also be of value for other applications than electrophoresis, such as e.g. chromatography.

Figure 2:
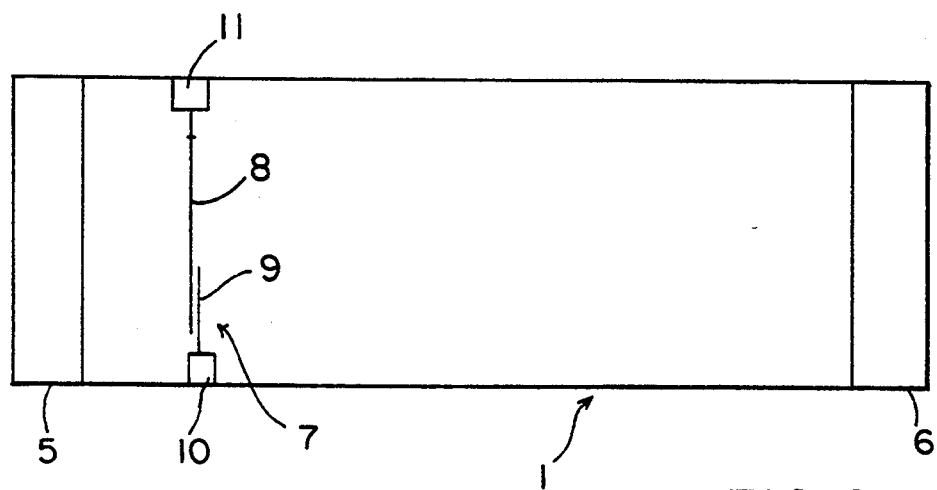
FIG. 2 is a plan view of one of the base layers of the structure in FIG. 1 including detector and electric contact means.
Figure 10:
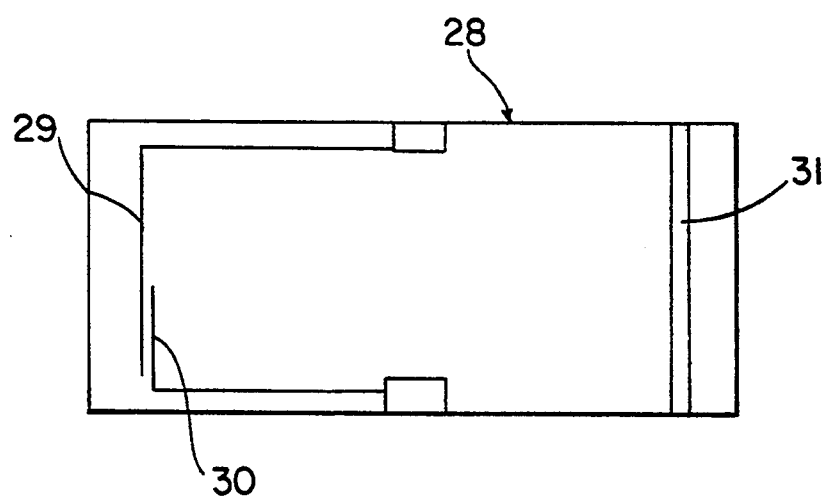
FIG. 10 is a schematic view of another embodiment of base layer including an ion exchanger strip.

Due to the resiliency of the spacing layer it will further be possible to provide for the injection of nanoliter quantity samples by a pumping action effected by varying the force that keeps the "sandwich" together. Also, the plate structure makes it possible to enrich sample molecules in an electrophoretic channel on a zone of e.g. an ion exchanger. An example of the provision of such an ion exchanger zone is given in FIG. 10 which illustrates an embodiment of a base layer corresponding to the base layer 1 in FIGS. 1, 2 and 5. As shown in the figure, the base plate 28 has, in addition to detector electrodes 29, 30, a thin strip 31 of an ion exchanger material. When performing the electrophoresis with, for example, an electrophoretic plate according to FIG. 5, the strip 31 is within the channel 4, and sample in suitable buffer applied through the channel inlet is first enriched in ion exchanger strip 31. Electrophoretic buffer is thereupon introduced to remove the excess of sample in the channel 4. The sample is then desorbed by the electrophoretic field or the pH shift generated thereby.

Figure 11:
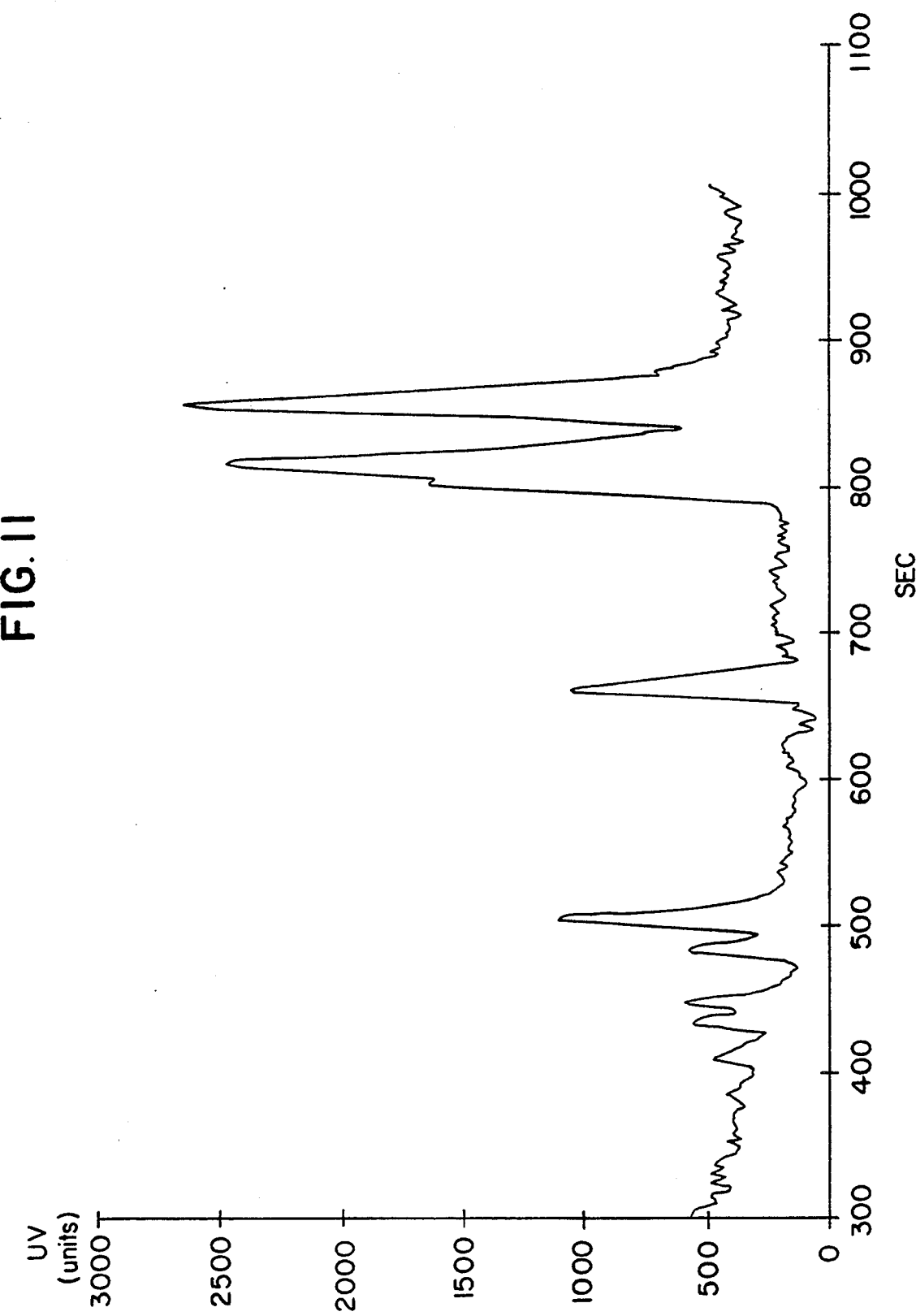
FIG. 11 is a diagram showing the result of an electrophoretic procedure performed with a capillary electrophoretic plate of the invention.

FIG. 11 illustrates an electropherogram obtained in an electrophoresis of a restriction digest of $\phi$X174 with Hae III performed with a Hostaflon electrophoretic plate produced as described above by coining against an etched silicon surface. The total channel length was 50 mm, the channel width was 250 μm, and the channel height was 50 μm. In use the plate was clamped between the flat surfaces of a clamping means with a total force of about 100N. The separation channel was hydrophilized with a non-ionic detergent and filled with 10% linear polyacrylamide as separation media and Tris-borate, pH 8.3, was used as buffer. Injection was electrokinetic at 5 sec/700 V, total potential drop 700 V. Detection was performed by UV at 260 nm.

The invention is, of course, not restricted to the specific embodiments described above and shown in the drawings, but many modifications and variations are within the scope of the general inventive concept as stated in the appended claims.

We claim:

1. A microfluidic structure, comprising:
first and second substantially planar form-stable base layers; and
a first intermediate spacing layer of elastic material, said first spacing layer being recessed to define a microcavity or channel system with at least one of said first and second base layers, said first spacing layer and at least one of said first and second base layers being made of the same material.

2. The structure of claim 1, wherein said first spacing layer is recessed through a thickness thereof such that side walls of the microcavity or channel system are formed by said first spacing layer and top and bottom walls are formed by said first and second base layers.

3. The structure of claim 1 or 2, wherein said first spacing layer is integral with one of said first and second base layers.

4. The structure of claim 3, wherein said first spacing layer fills part of a space between said first and second base layers and only forms wall members of the channel or microcavity defined by said structure.

5. The structure of claim 1, wherein at least one of said first and second base layers is flexible.

6. The structure of claim 1, wherein at least one of said first and second base layers is rigid.

7. The structure of claim 1, wherein said first spacing layer fills part of a space between said first and second base layers and only forms wall members of the channel or microcavity defined by said structure.

8. The structure of claim 1, wherein said structure is a plate for capillary electrophoresis.

9. The structure of claim 8, further comprising detector means arranged on one side of said first and second base layers.

10. The structure of claim 1, further comprising a second spacing layer, separated by said first and second base layers and a third base layer the channel or microcavity of said first spacing layer being connected to a channel or microcavity of said second spacing layer by a bore in an intermediate base layer.

11. The structure of claim 10, further comprising at least she additional spacing layer and base layer combination on top of said third base layer.

12. A process of producing a microfluidic structure, comprising the steps of:
(i) providing a planar mold surface having a relief pattern corresponding to a desired spacing layer geometry,
(ii) molding a spacing layer of elastic material against said planar mold surface, and
(iii) after removal from the mold, applying first and second substantially planar form-stable base layers to opposite sides of the spacing layer such that a channel or microcavity system is defined by the spacing layer with at least one of said first and second base layers.

13. The process of claim 12, further comprising the step of:
applying at least one additional spacing layer and base layer the produced structure.

14. A process of producing a microfluidic structure comprising the steps of:
(a) providing a planar mold surface having a relief pattern corresponding to a desired spacing layer geometry,
(b) molding a spacing layer of elastic material against said planar mold surface, the spacing layer being attached to or integral with a first substantially planar form-stable base layer, and
(c) after removal from the mold, applying a second substantially planar form-stable base layer to the opposite side of the spacing layer, such that a channel or microcavity system is defined by the spacing layer with at least one of said first and second base layers.

15. The process of claim 14, further comprising the step of:
(d) molding at least two base layer supported spacing layers, stacked on top of each other, and applying said second base layer.

16. The process of claim 12 or 14, wherein said relief pattern of the mold surface is produced by etching.

17. The process of claim 12 or 14, wherein said mold is made of single-crystalline silicon.

18. A process of producing a microfluidic structure comprising the steps of:
a) providing a planar mold having a relief pattern corresponding to a desired spacing layer geometry;
b) applying a first base layer against the planar mold;
c) injecting a cross-linkable polymer liquid or thermoplastic polymer melt into a cavity defined between a surface of the planar mold and the base layer (2);
d) stabilizing said injected polymer by cross-linking or temperature reduction;
e) removing the base layer and spacing layer from the planar mold; and
f) applying a second base layer to the spacing layer of said structure.

19. The process of claim 18, further comprising the step of:
(a) molding at least two base layer supported spacing layers, stacked on top of each other, and applying said second base layer.

20. The process of claim 19, wherein said cross-linking is effected by photo-initiation.

21. The process according of claim 19, wherein said relief pattern of the mold surface is produced by etching.

22. The process claim 19, wherein said mold is made of single-crystalline silicon.

23. A process of producing a microfluidic structure comprising the steps of:
a) providing a planar mold having a relief pattern corresponding to a desired spacing layer geometry;
b) applying a cross-linkable or thermoplastic spacing layer material, against the planar mold and pressing the spacing layer and the planar mold together;
c) stabilizing the spacing layer formed by cross-linking or temperature reduction;
d) removing the spacing layer from the mold; and
e) applying first and second base layers to opposite sides of the spacing layer.

24. The process of claim 23, further comprising the step of:
(f) applying at least one additional spacing layer and base layer to the produced structure.

25. A process of producing a microfluidic structure comprising the steps:
a) providing a planar mold having a relief pattern corresponding to a desired spacing layer geometry;
b) applying a cross-linkable or thermoplastic spacing layer material supported by or integral with a first base layer against the planar mold and pressing the spacing layer and the planar mold together;
c) stabilizing the spacing layer formed by cross-linking or temperature reduction;
d) removing the spacing layer and the first base layer from the mold; and
e) applying a second base layer to the spacing layer.

26. The process of claim 25, further comprising the step of:
(f) producing at least two base layer supported spacing layers, stacked on top of each other, and applying said second base layer.

27. The process of claim 23 or 25, wherein said cross-linking is effected by photo-initiation.

28. The process of claim 23 or 25, wherein said relief pattern of the mold surface is produced by etching.

29. The process of claim 23 or 25, wherein said mold is made of single-crystalline silicon.

30. The process of claim 23 or 25, wherein in step (b), the spacing layer and the planar mold are heated.

* * * * *

UNITED STATES PATENT AND TRADEMARK OFFICE
CERTIFICATE OF CORRECTION

PATENT NO. : 5,376,252
DATED : December 27, 1994
INVENTOR(S) : Ekstrom et al.

It is certified that error appears in the above-identified patent and that said Letters Patent is hereby corrected as shown below:

```
On the title page, items
[22] --PCT Filed:   May 8, 1991--

--[86] PCT No.:  PCT/SE91/00327

§371 Date:     November 10, 1992

§102(e) Date: November 10, 1992--

--[87] PCT Pub. No.:    WO91/16966

PCT Pub. Date:   November 14, 1991--
```

Signed and Sealed this

Thirty-first Day of October 1995

Attest:

BRUCE LEHMAN

Attesting Officer        Commissioner of Patents and Trademarks

(12) EX PARTE REEXAMINATION CERTIFICATE (8131st)
United States Patent
Ekström et al.

(10) Number: US 5,376,252 C1
(45) Certificate Issued: Apr. 5, 2011

(54) MICROFLUIDIC STRUCTURE AND PROCESS FOR ITS MANUFACTURE

(75) Inventors: Björn Ekström, Upsala (SE); Gunilla Jacobson, Upsala (SE); Ove Ohman, Upsala (SE); Hakan Sjödin, Upsala (SE)

(73) Assignee: Lagrummet December 1047 AB, Uppsala (SE)

Reexamination Request:
No. 90/009,758, Jun. 28, 2010

Reexamination Certificate for:
Patent No.: 5,376,252
Issued: Dec. 27, 1994
Appl. No.: 07/946,332
Filed: Nov. 10, 1992

Certificate of Correction issued Oct. 31, 1995.

(22) PCT Filed: May 8, 1991
(86) PCT No.: PCT/SE91/00327
§ 371 (c)(1),
(2), (4) Date: Nov. 10, 1992
(87) PCT Pub. No.: WO91/16966
PCT Pub. Date: Nov. 14, 1991

(51) Int. Cl.
*B29C 33/42* (2006.01)
*B29C 35/08* (2006.01)
*B29C 45/00* (2006.01)
*B01D 57/02* (2006.01)
*B01L 3/00* (2006.01)
*B29D 24/00* (2006.01)
*G01N 27/447* (2006.01)
*G01N 30/00* (2006.01)
*G01N 30/60* (2006.01)

(52) U.S. Cl. ............ 204/603; 204/604; 210/198.2; 210/656; 422/947; 73/23.39; 73/61.53
(58) Field of Classification Search .............. None
See application file for complete search history.

(56) References Cited

U.S. PATENT DOCUMENTS

| 3,565,537 A | 2/1971 | Fielding |
| 3,690,836 A | 9/1972 | Buissiere |
| 3,867,201 A | 2/1975 | Holmes |
| 3,992,158 A | 11/1976 | Przybylowicz et al. |
| 4,353,858 A | 10/1982 | Gilleo |

(Continued)

FOREIGN PATENT DOCUMENTS

| FR | 1444146 A | 7/1966 |
| WO | WO-90/04645 A1 | 5/1990 |

(Continued)

OTHER PUBLICATIONS

European Search Report in EP Application No. 79302339 dated Jan. 1, 1980.

(Continued)

*Primary Examiner*—Terrence R Till

(57) ABSTRACT

The microfluidic structure comprises first and second substantially planar form-stable base layers and an intermediate spacing layer of elastic material, said spacing layer being recessed to define a microcavity or channel system with at least one of said first and second base layers. The structure is produced by moulding the spacing layer, optionally applied to or integral with a first base layer, against a planar mould, and the microcavity or channel system is completed by applying a second base layer, and optionally said first base layer, to the spacing layer.

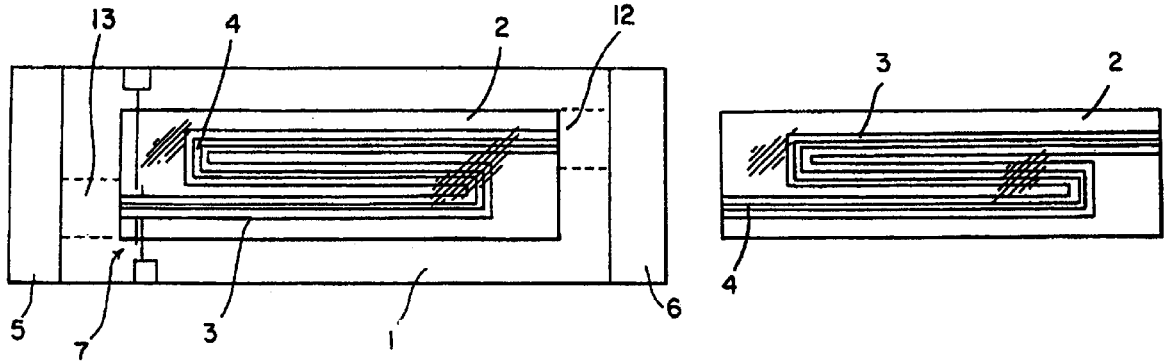

U.S. PATENT DOCUMENTS

| | | | |
|---|---|---|---|
| 4,392,362 | A | 7/1983 | Little |
| 4,756,884 | A | 7/1988 | Hillman et al. |
| 5,035,139 | A | 7/1991 | Hoefelmayr et al. |
| 5,135,478 | A | 8/1992 | Sibalis |
| 5,137,817 | A | 8/1992 | Busta et al. |
| 5,208,145 | A | 5/1993 | Rogers |
| 5,376,252 | A | 12/1994 | Ekstrom et al. |
| 5,449,492 | A | 9/1995 | Krishtal |
| 5,501,662 | A | 3/1996 | Hofmann |
| 5,597,699 | A | 1/1997 | Lanzara |
| 6,184,029 | B1 | 2/2001 | Wilding et al. |
| 2002/0076689 | A1 | 6/2002 | Farb et al. |

FOREIGN PATENT DOCUMENTS

| | | |
|---|---|---|
| WO | WO-94/20841 A1 | 9/1994 |
| WO | WO-95/23211 A1 | 8/1995 |
| WO | WO-96/00111 A1 | 1/1996 |
| WO | WO-96/10170 A1 | 4/1996 |
| WO | WO-96/13721 A1 | 5/1996 |
| WO | WO-97/05922 A2 | 2/1997 |

OTHER PUBLICATIONS

Fishman et al., "Identification of receptor ligands and receptor subtypes using antagonists in a capillary electrophoresis single–cell biosensor separation system", Proc. Natl. Acad. Sci. USA, vol. 92, pp. 7877–7881, Aug. 1995.

Hamill et al., "Improved Patch–Clamp Techniques for High–Resolution Current Recording from Cells and Cell–Free Membrane Patches", Pflugers Archiv (1981) 391:85, pp. 100–104.

International Preliminary Examination Report in PCT/SE91/00327 dated Jul. 24, 1992.

International Search Report in PCT/SE91/00327 dated Jul. 30, 1991.

Pihl et al., "Microfluidic gradient–generating device for pharmacological profiling." Analytical Chemistry Jul. 1, 2005, vol. 77, No. 13, Jul. 1, 2005 (Jul. 1, 2005), pp. 3897–390.

Reexamination Request for U.S. Patent No. 5,376,252 and appendices.

Reexamination Request for U.S. Patent No. 7,390,650 and appendices.

Reexamination Request for U.S. Patent No. 7,470,518 and appendices.

Reexamination Request for U.S. Patent No. 7,563,614 and appendices.

Second Amended Complaint for Patent Infringement of U.S. Patent Nos. 5,376,252, 7,390,650, 7,470,518, and 7,563,614 in *Cellectricon AB. et al.* v. *Fluxion Biosciences, Inc.,* Case No. 5:09–cv–0315 (RMW).

Cellectricon AB's and Gyros AB's Answer to Defendant's Counterclaims and Affirmative Defenses in *Cellectricon AB. et al.* v. *Fluxion Biosciences, Inc.,* Case No. 5:09–cv–0315 (RMW).

Fluxion Biosciences, Inc's Answer and Counterclaims to Second Amended Complaint in *Cellectricon AB. et al.* v. *Fluxion Biosciences, Inc.,* Case No. 5:09–cv–0315 (RMW).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7, 12, 14, 23, 25 and 30 is confirmed.

Claims 8-11, 13, 15-22, 24 and 26-29 were not reexamined.

\* \* \* \* \*

(12) EX PARTE REEXAMINATION CERTIFICATE (9299th)
United States Patent
Ekström et al.

(10) Number: US 5,376,252 C2
(45) Certificate Issued: Sep. 11, 2012

(54) MICROFLUIDIC STRUCTURE AND PROCESS FOR ITS MANUFACTURE

(75) Inventors: Björn Ekström, Upsala (SE); Gunilla Jacobson, Upsala (SE); Ove Ohman, Upsala (SE); Hakan Sjödin, Upsala (SE)

(73) Assignee: Cellectricon AB, Molndal (SE)

Reexamination Request:
No. 90/009,913, Jun. 17, 2011

Reexamination Certificate for:
Patent No.: 5,376,252
Issued: Dec. 27, 1994
Appl. No.: 07/946,332
Filed: Nov. 10, 1992

Reexamination Certificate C1 5,376,252 issued Apr. 5, 2011

Certificate of Correction issued Oct. 31, 1995.

(22) PCT Filed: May 8, 1991

(86) PCT No.: PCT/SE91/00327

§ 371 (c)(1), (2), (4) Date: Nov. 10, 1992

(87) PCT Pub. No.: WO91/16966

PCT Pub. Date: Nov. 14, 1991

(30) Foreign Application Priority Data

May 10, 1990 (SE) .............................................. 9001699

(51) Int. Cl.
| | |
|---|---|
| *B29C 33/42* | (2006.01) |
| *B29C 35/08* | (2006.01) |
| *B29C 45/00* | (2006.01) |
| *B01D 57/02* | (2006.01) |
| *B01L 3/00* | (2006.01) |
| *B29D 24/00* | (2006.01) |
| *G01N 27/447* | (2006.01) |
| *G01N 30/00* | (2006.01) |
| *G01N 30/60* | (2006.01) |

(52) U.S. Cl. ...................... 204/603; 204/604; 210/198.2; 210/656; 422/947; 73/23.39; 73/61.53

(58) Field of Classification Search ........................ None
See application file for complete search history.

(56) References Cited

To view the complete listing of prior art documents cited during the proceeding for Reexamination Control Number 90/009,913, please refer to the USPTO's public Patent Application Information Retrieval (PAIR) system under the Display References tab.

*Primary Examiner* — Terrence Till

(57) ABSTRACT

The microfluidic structure comprises first and second substantially planar form-stable base layers and an intermediate spacing layer of elastic material, said spacing layer being recessed to define a microcavity or channel system with at least one of said first and second base layers. The structure is produced by moulding the spacing layer, optionally applied to or integral with a first base layer, against a planar mould, and the microcavity or channel system is completed by applying a second base layer, and optionally said first base layer, to the spacing layer.

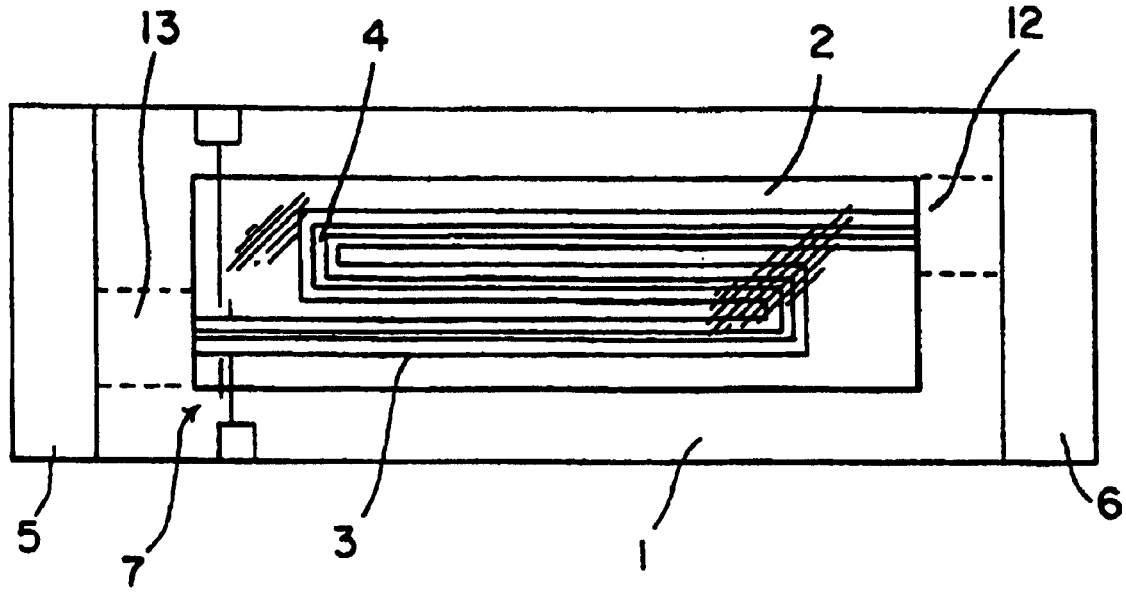

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 8-11, 13 and 15 is confirmed.

Claims 1-7, 12, 14, 16-18, 23 and 25 are cancelled.

Claims 19-22, 24 and 26-30 were not reexamined.

* * * * *